(12) United States Patent
Ivosevic et al.

(10) Patent No.: US 12,661,041 B2
(45) Date of Patent: Jun. 23, 2026

(54) CAP WITH VENTING PLUG FOR BIOLOGICAL FLUID COLLECTION DEVICE

(71) Applicant: Becton, Dickinson and Company, Franklin Lakes, NJ (US)

(72) Inventors: Milan Ivosevic, Kinnelon, NJ (US); Ryan W. Muthard, Wynnewood, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 609 days.

(21) Appl. No.: 17/051,107

(22) PCT Filed: Apr. 30, 2019

(86) PCT No.: PCT/US2019/029926
§ 371 (c)(1),
(2) Date: Oct. 27, 2020

(87) PCT Pub. No.: WO2019/213089
PCT Pub. Date: Nov. 7, 2019

(65) Prior Publication Data
US 2021/0236029 A1 Aug. 5, 2021

Related U.S. Application Data

(60) Provisional application No. 62/665,092, filed on May 1, 2018.

(51) Int. Cl.
*A61B 5/15* (2006.01)

(52) U.S. Cl.
CPC .... *A61B 5/150351* (2013.01); *A61B 5/15003* (2013.01); *A61B 5/150213* (2013.01);
(Continued)

(58) Field of Classification Search
CPC .......... A61B 5/150351; A61B 5/15003; A61B 5/150213; A61B 5/150343; A61B 5/150755; A61B 2560/04
See application file for complete search history.

(56) References Cited

U.S. PATENT DOCUMENTS 4,803,999 A * 2/1989 Liegner ............ A61B 5/150992
600/576
5,125,415 A 6/1992 Bell
(Continued)

FOREIGN PATENT DOCUMENTS

JP S61174905 U 10/1986
JP H4231967 8/1992
(Continued)

*Primary Examiner* — Charles A Marmor, II
*Assistant Examiner* — Severo Antonio P Lopez
(74) *Attorney, Agent, or Firm* — The Webb Law Firm

(57) ABSTRACT

A cap with a venting plug for a biological fluid collection device is disclosed. The venting plug allows air to pass therethrough and prevents a blood sample from passing therethrough. In one embodiment, the venting plug is a porous plug. In one embodiment, the cap includes a venting plug including a carboxymethylcellulose additive. A cap that limits analyte bias due to the interaction of plasma ions with the carboxymethylcellulose by reducing the contact area between the blood and the carboxymethylcellulose additive, e.g., decreasing radius, is also disclosed.

7 Claims, 12 Drawing Sheets

(52) U.S. Cl.
CPC .. *A61B 5/150343* (2013.01); *A61B 5/150755* (2013.01); *A61B 2560/04* (2013.01)

(56) References Cited

U.S. PATENT DOCUMENTS

| | | | |
|---|---|---|---|
| 7,160,267 B2 | 1/2007 | Brown | |
| 2003/0236497 A1* | 12/2003 | Fremming | ....... A61B 5/150519 |
| | | | 604/126 |
| 2005/0043650 A1 | 2/2005 | Sarstedt | |
| 2005/0065454 A1* | 3/2005 | Manoussakis | ... A61B 5/150213 |
| | | | 600/576 |
| 2005/0273019 A1 | 12/2005 | Conway et al. | |
| 2006/0009727 A1* | 1/2006 | O'Mahony | ......... A61M 1/3468 |
| | | | 604/4.01 |
| 2008/0312576 A1 | 12/2008 | McKinnon et al. | |
| 2009/0071911 A1* | 3/2009 | Folden | ................ A61M 1/3641 |
| | | | 210/188 |
| 2009/0259145 A1 | 10/2009 | Bartfeld et al. | |
| 2014/0030754 A1 | 1/2014 | Craft et al. | |
| 2016/0262679 A1* | 9/2016 | Ivosevic | .......... A61B 5/150755 |
| 2016/0367177 A1 | 12/2016 | Edelhauser et al. | |
| 2017/0216835 A1 | 8/2017 | Ivosevic et al. | |

FOREIGN PATENT DOCUMENTS

| | | | |
|---|---|---|---|
| JP | 2017531782 A | 10/2017 | |
| RU | 2299680 C2 | 5/2007 | |
| WO | 2016205779 A2 | 12/2016 | |

* cited by examiner

SEE FIG. 3

20

44

20

44

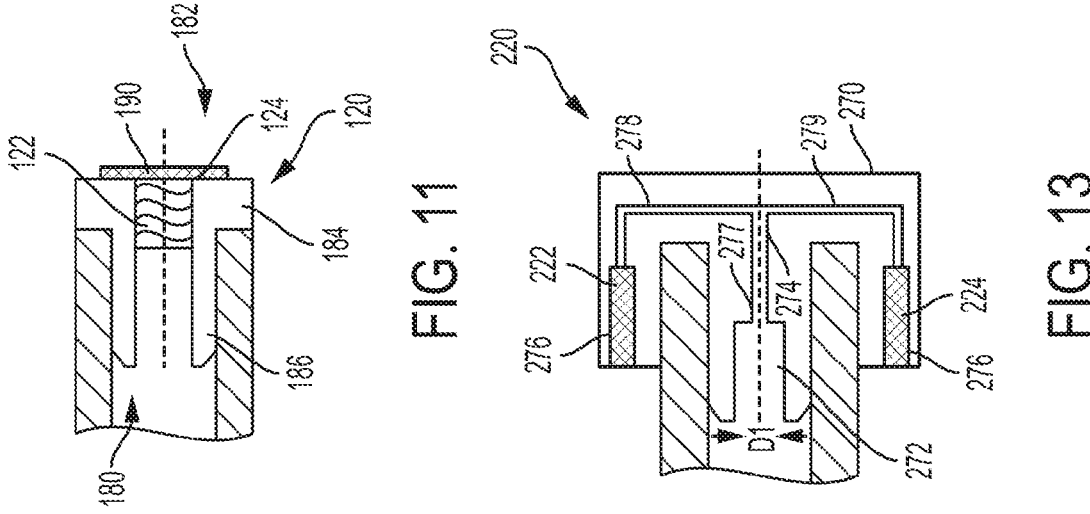
FIG. 10
FIG. 11
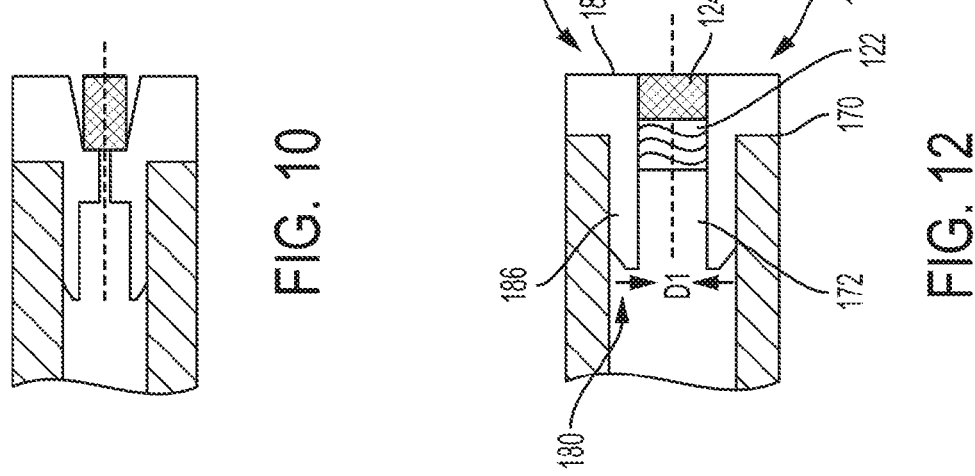
FIG. 12
FIG. 13

CAP WITH VENTING PLUG FOR BIOLOGICAL FLUID COLLECTION DEVICE

CROSS-REFERENCE TO RELATED APPLICATIONS

This application is the United States national phase of International Application No. PCT/US2019/029926 filed Apr. 30, 2019, and claims priority to United States Provisional Application Ser. No. 62/665,092, entitled "Cap with Venting Plug for Biological Fluid Collection Device", and filed May 1, 2018, the entire disclosures of which are hereby incorporated by reference in their entirety.

BACKGROUND OF THE INVENTION

1. Field of the Disclosure

The present disclosure relates generally to a biological fluid collection device. More particularly, the present disclosure relates to a cap with a venting plug for a biological fluid collection device.

2. Description of the Related Art

Caps are needed to seal collection chambers of biological fluid collection devices. Collection chambers need to have air vented prior to sealing liquids within the chamber. One of the key applications of such caps is to seal a biological fluid collection device following the removal of the systems residual air. This has two primary impacts on sample collection. First, blood gas measurements must be performed with blood that has been collected anaerobically (no air). Second, air removal facilitates the collection of a full sample volume rather than a fraction of the available volume due to the presence of air pockets. Both of these impacts are critical for a properly anticoagulated and bias free blood sample.

SUMMARY OF THE INVENTION

The present disclosure provides a cap with a venting plug for a biological fluid collection device. The venting plug allows air to pass therethrough and prevents a blood sample from passing therethrough. In one embodiment, the venting plug is a porous plug. In one embodiment, the cap includes a venting plug including a carboxymethylcellulose additive.

The present disclosure provides, in one embodiment, a cap that limits analyte bias due to the interaction of plasma ions with the carboxymethylcellulose by reducing the contact area between the blood and the carboxymethylcellulose additive, e.g., decreasing radius. The present disclosure provides, in one embodiment, a cap that limits analyte bias due to the interaction of plasma ions with the carboxymethylcellulose by increasing the path length between the blood and the carboxymethylcellulose additive, e.g., increasing a path length. The present disclosure provides, in one embodiment, a cap that limits analyte bias due to the interaction of plasma ions with the carboxymethylcellulose by reducing diffusivity by introducing a porous material in front of the carboxymethylcellulose additive plug.

In accordance with an embodiment of the present invention, a cap for a biological fluid collection device includes a cap body defining a first chamber having a first diameter, a second chamber having a second diameter, and a third chamber having a third diameter, the second chamber between the first chamber and the third chamber; and a venting plug disposed in the third chamber, the venting plug comprising a carboxymethylcellulose additive, wherein the second diameter is less than the first diameter, and wherein the second diameter is less than the third diameter.

In one configuration, the venting plug allows air to pass therethrough and prevents a blood sample from passing therethrough. In another configuration, the venting plug is a porous plug. In yet another configuration, the first diameter is less than the third diameter. In one configuration, the first diameter is 1.016 mm, the second diameter is 0.4 mm, and the third diameter is 1.5 mm. In another configuration, a length of the second chamber is 1.6 mm and a length of the third chamber is 3.5 mm. In yet another configuration, the cap body has a front end and a back end. In one configuration, the first chamber is adjacent the front end of the cap body. In another configuration, the third chamber is adjacent the back end of the cap body. In yet another configuration, the cap body includes a flange portion and a plug portion.

In accordance with another embodiment of the present invention, a cap for a biological fluid collection device includes a cap body defining a chamber having a first diameter, the cap body having a front end and a back end; a first venting plug disposed in the chamber; and a second venting plug comprising a carboxymethylcellulose additive, wherein the first venting plug is disposed between the second venting plug and the front end of the cap body.

In one configuration, the second venting plug allows air to pass therethrough and prevents a blood sample from passing therethrough. In another configuration, the second venting plug is a porous plug. In yet another configuration, the first venting plug is a porous plug. In one configuration, the second venting plug is disposed in the chamber. In another configuration, the second venting plug is a sheet that covers a portion of the back end of the cap body. In yet another configuration, the cap body includes a flange portion and a plug portion.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 10 is a cross-sectional view of a cap with venting plug in accordance with another embodiment of the present invention.

FIG. 11 is a cross-sectional view of a cap with venting plug in accordance with another embodiment of the present invention.

FIG. 12 is a cross-sectional view of a cap with venting plug in accordance with another embodiment of the present invention.

FIG. 13 is a cross-sectional view of a cap with venting plug in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figures 1, 2:
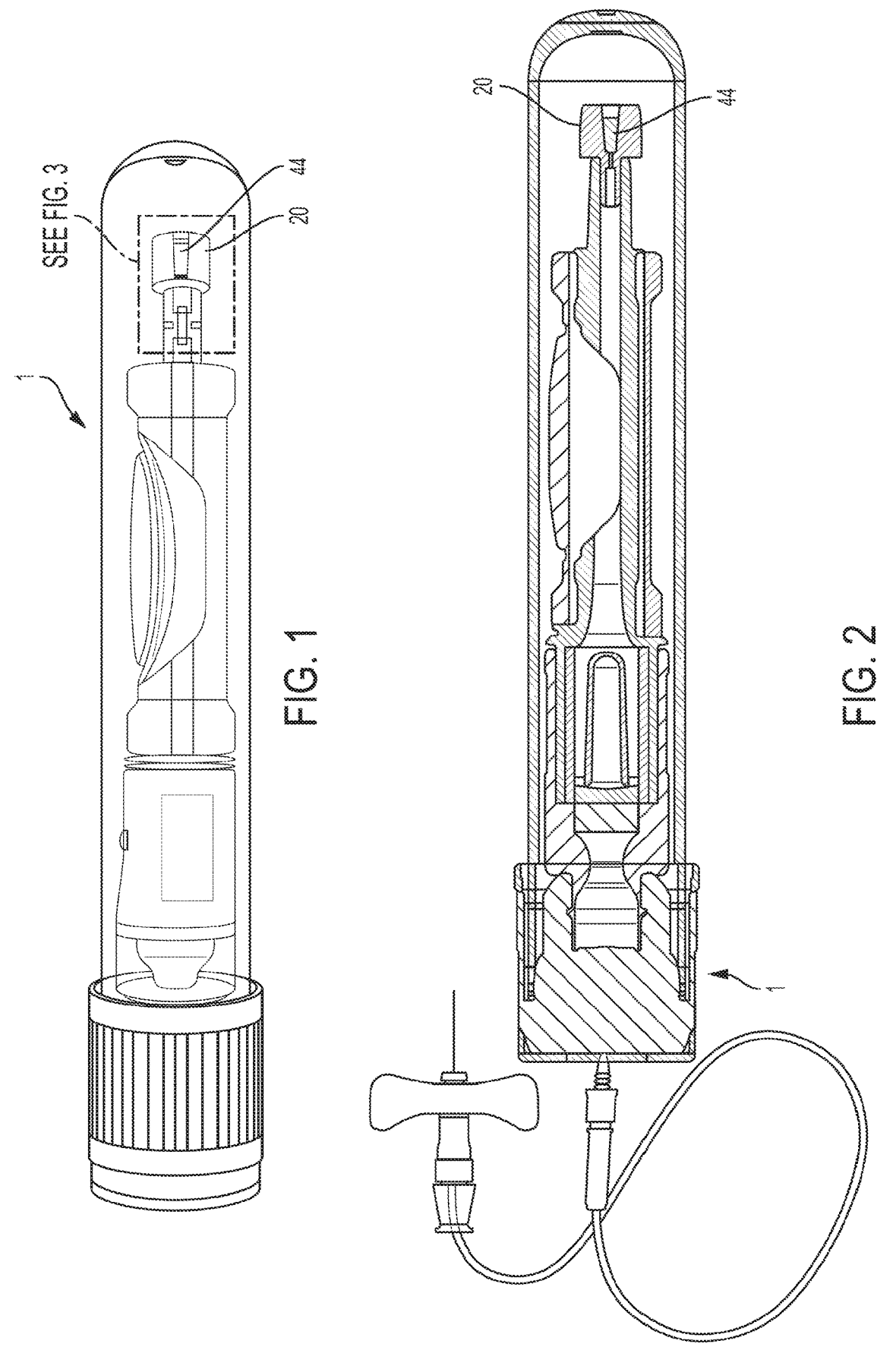
FIG. 1 is a perspective view of a biological fluid collection device with cap in accordance with an embodiment of the present invention.
FIG. 2 is a perspective view of a biological fluid collection device with cap in accordance with an embodiment of the present invention.
Figure 3:
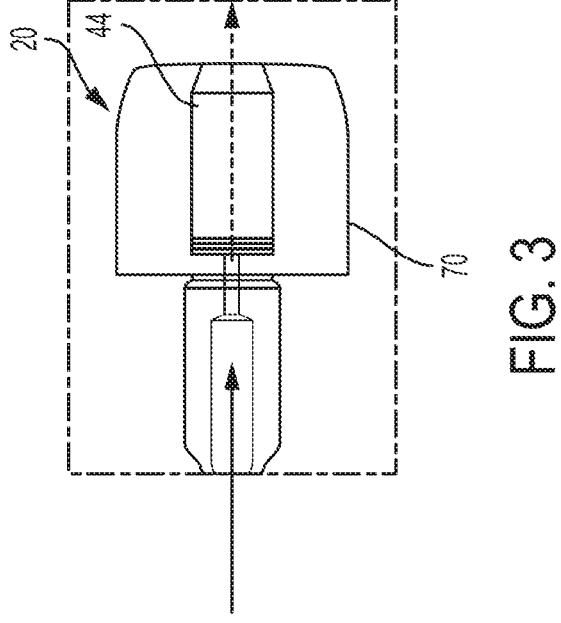
FIG. 3 is a perspective view of a cap in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides a cap with a venting plug for a biological fluid collection device. The venting plug allows air to pass therethrough and prevents a blood sample from passing therethrough. In one embodiment, the venting plug is a porous plug. In one embodiment, the cap includes a venting plug including a carboxymethylcellulose additive.

Carboxymethylcellulose is a "self-sealing" additive that swells when it comes into contact with a liquid. When this additive is placed within a porous material, particularly a hydrophobic material, it allows air to vent prior to swelling shut when liquid reaches the carboxymethylcellulose. This prevents liquid from escaping a collection chamber of the biological fluid collection device. Carboxymethylcellulose can cause analyte bias (typically $Ca^{2+}$, $Na^+$, $K^+$) in small blood sample volumes (<5 mL).

If membranes having a carboxymethylcellulose additive are exposed to blood, or liquids of interest, at a high surface area contact area to volume ratio can drastically impact analyte bias results in blood. The ion exchange that occurs between the carboxymethylcellulose additive and the ions in plasma can result in erroneous results.

In one embodiment, a cap of the present disclosure limits analyte bias due to the interaction of plasma ions with the carboxymethylcellulose by reducing the contact area between the blood and the carboxymethylcellulose additive, e.g., decreasing radius.

In one embodiment, a cap of the present disclosure limits analyte bias due to the interaction of plasma ions with the carboxymethylcellulose by increasing the path length between the blood and the carboxymethylcellulose additive, e.g., increasing a path length.

In one embodiment, a cap of the present disclosure limits analyte bias due to the interaction of plasma ions with the carboxymethylcellulose by reducing diffusivity by introducing a porous material in front of the carboxymethylcellulose additive plug.

A cap of the present disclosure reduces the rate at which a biasing ion can travel away from the carboxymethylcellulose source into the blood, i.e., measurement sample. A cap of the present disclosure is of particular interest in small blood volumes (<5 mL) where the carboxymethylcellulose additive can drastically impact ion concentrations.

The present disclosure provides a cap with a venting plug for a biological fluid collection device. A cap of the present disclosure is compatible with a biological fluid collection device 1 as shown in FIGS. 14-21.

Figure 15:
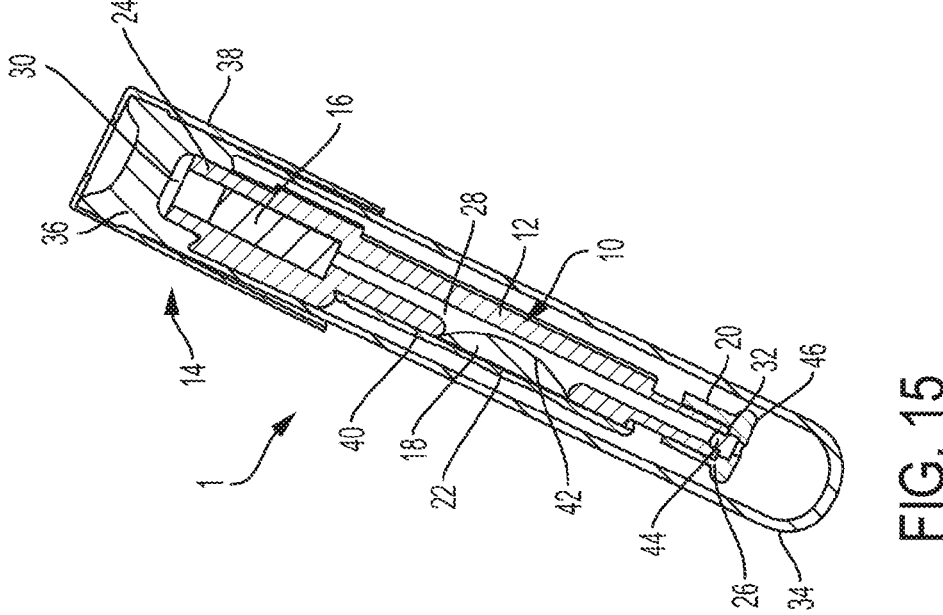
FIG. 15 is a partial cross-sectional perspective view of the biological fluid collection device of FIG. 14 in accordance with an embodiment of the present invention.
Figure 14:
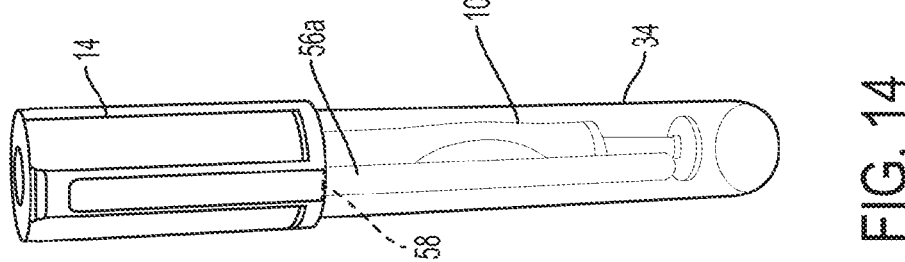
FIG. 14 is a perspective view of a biological fluid collection device having a collection module disposed within an outer housing in accordance with an embodiment of the present invention.
Figure 14:

Referring to FIGS. 14 and 15, in one embodiment, a biological fluid collection device 1 includes a collection module 10 disposed within an outer housing 34. The collection module 10 is adapted to receive a biological fluid sample, such as a blood sample, and includes a housing 12, a closure 14, a mixing chamber 16, a holding chamber 18, a cap 20, and an activation member 22.

In one embodiment, the housing 12 includes a first end 24, a second end 26, and a passageway 28 extending therebetween and providing fluid communication between the first end 24 and the second end 26 of the housing 12. The passageway 28 has a sample introduction opening 30 at the first end 24 of the housing 12 and a sample dispensing opening 32 at the second end 26 of the housing 12. The mixing chamber 16 and the holding chamber 18 are provided in fluid communication with the passageway 28. The mixing chamber 16 and the holding chamber 18 are positioned such that a biological fluid sample, such as a blood sample, introduced into the sample introduction opening 30 of the passageway 28 will first pass through the mixing chamber 16 and subsequently pass into the holding chamber 18, prior to reaching the sample dispensing opening 32 of the passageway 28. In this way, the blood sample may be mixed with an anticoagulant or other additive provided within the mixing chamber 16 before the stabilized sample is received and stored within the holding chamber 18.

The mixing chamber 16 allows for passive mixing of the blood sample with an anticoagulant or another additive, such as a blood stabilizer, as the blood sample flows through the passageway 28. The internal portion of the mixing chamber 16 may have any suitable structure or form as long as it provides for the mixing of the blood sample with an anticoagulant or another additive as the blood sample passes through the passageway 28. The mixing chamber 16 may include a dry anticoagulant, such as Heparin or EDTA, deposited on or within the mixing chamber 16. The mixing chamber 16 may, for example, include an open cell foam containing dry anticoagulant dispersed within the cells of the open cell foam to promote the effectiveness of the flow-through mixing and anticoagulant uptake.

The open cell foam may be treated with an anticoagulant to form a dry anticoagulant powder finely distributed throughout the pores of the open cell foam. As the blood sample enters the mixing chamber 16, the blood sample passes through the open cell foam and is exposed to the anticoagulant powder available throughout the internal pore structure of the open cell foam.

The open cell foam may be a soft deformable open cell foam that is inert to blood, for example, a melamine foam, such as Basotect® foam commercially available from BASF, or may consist of a formaldehyde-melamine-sodium bisulfite copolymer. The open cell foam may also be a flexible, hydrophilic open cell foam that is substantially resistant to heat and organic solvents. In one embodiment, the foam may include a sponge material.

The anticoagulant or other additive may be introduced into the open cell foam by soaking the foam in a liquid solution of the additive and water and subsequently evaporating the water forming a dry additive powder finely distributed throughout the internal structure of the foam.

After passing through the mixing chamber 16, the blood sample may be directed to the holding chamber 18. The holding chamber 18 may take any suitable shape and size to store a sufficient volume of blood necessary for the desired testing, for example 500 μl or less. In one embodiment, the holding chamber 18 is defined by a portion of the housing 12 in combination with an elastic sleeve 40 secured about the exterior of the housing 12. The elastic sleeve 40 may be made of any material that is flexible, deformable, and capable of providing a fluid tight seal with the housing 12, including, but not limited to, natural or synthetic rubber, and other suitable elastomeric materials. The housing 12 includes a recess 42 that extends from the exterior of the housing 12 to the passageway 28 effectively creating an opening in the housing 12 in fluid communication with the passageway 28. The elastic sleeve 40 covers the recess 42 defining the holding chamber 18 having an internal fill volume of 500 μl or less.

A cap 20 disposed at the second end 26 of the housing 12 covers the sample dispensing opening 32 of the passageway 28. Referring to FIGS. 1-5, a cap 20 of the present disclosure includes a venting plug 44 that allows air to pass therethrough and prevents a blood sample from passing therethrough. In one embodiment, the venting plug 44 is a porous plug. In one embodiment, the cap 20 includes a venting plug 44 that includes a carboxymethylcellulose additive.

Referring to FIG. 15, in one embodiment, the cap 20 includes a venting plug 44, such as a porous plug, extending from the interior surface of the cap 20 to the exterior surface of the cap 20. The construction of the venting plug 44 allows air to pass through the cap 20 while preventing the blood sample from passing through the cap 20 and may include a hydrophobic filter. The venting plug 44 has selected air passing resistance that may be used to finely control the filling rate of the passageway 28. By varying the porosity of the plug, the velocity of the air flow out of the cap 20, and thus the velocity of the blood sample flow into the collection module 10, may be controlled. If the blood sample flow velocity into the collection module 10 is too fast, hemolysis may occur. If the blood sample flow velocity into the collection module 10 is too slow, sample collection time may be excessive.

A closure 14 is engaged with the first end 24 of the housing 12 to seal the passageway 28. The closure 14 allows for introduction of a blood sample into the passageway 28 of the housing 12 and may include a pierceable self-sealing stopper 36 with an outer shield 38 such as a Hemogard™ cap commercially available from Becton, Dickinson and Company. The closure 14 also secures to the outer housing 34 which may be a vacuum containing blood collection tube such as a Vacutainer® blood collection tube commercially available from Becton, Dickinson and Company.

Figure 20:
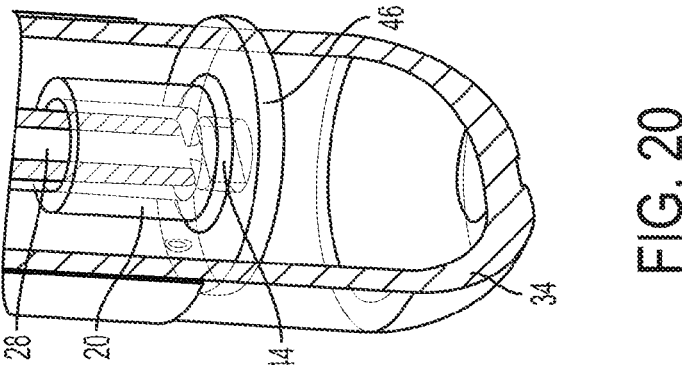
FIG. 20 is a partial cross-sectional perspective view of the lower end of a biological fluid collection device in accordance with an embodiment of the present invention.
Figure 19:
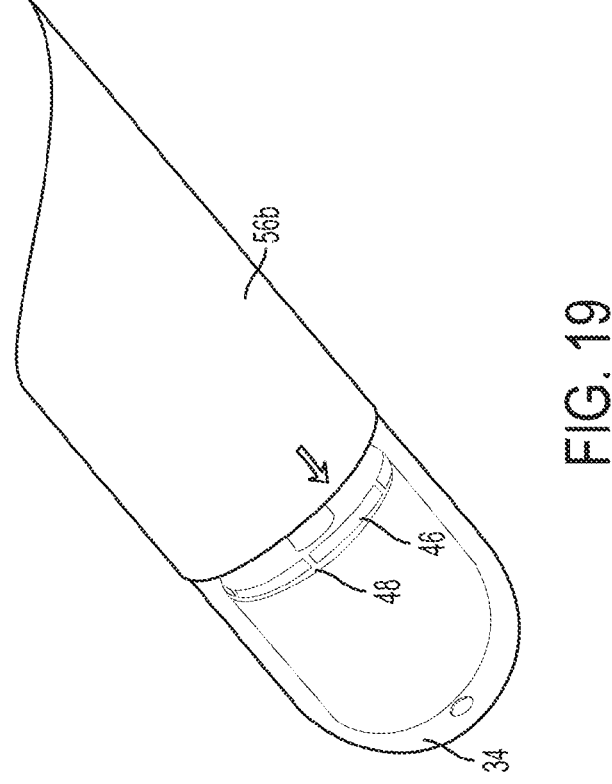
FIG. 19 is a partial perspective view of the lower end of a biological fluid collection device having a biological fluid collection module disposed within an outer collection housing in accordance with an embodiment of the present invention.

The cap 20 disposed at the second end 26 of the housing 12 may also include a flange 46 to assist the user in removing the cap 20 from the housing 12. As shown in FIG. 15, the flange 46 may have an outer diameter that is less than the inner diameter of the outer housing 34 in which the collection module 10 may be placed. Alternatively, as shown in FIGS. 19 and 20, the flange 46 may have an outer diameter substantially equal to the inner diameter of the outer housing 34. In this configuration, the flange 46 may include recesses or slots 48 extending from an upper surface to a lower surface to allow a vacuum within the outer housing 34 to pass around the flange 46. In addition, as shown in FIGS. 19 and 20, the flange 46 may be made of an optically clear material and may have a convex outer diameter surface such that it magnifies the venting plug 44 area of the cap 20 allowing a medical practitioner to see when the blood sample has fully filled the passageway 28 and reached the cap 20. The flange 46 may also be engaged with a recess of the interior wall of the outer housing 34 to restrain the cap 20 therewith.

In use, a needle cannula 50 (FIGS. 18A and 18C) is inserted into the passageway 28 of the housing 12 through the sample introduction opening 30, such as through the pierceable self-sealing stopper 36 of closure 14. As shown in FIG. 18A, the combined collection module 10 and the outer housing 34 may be inserted into a conventional tube holder 52 having a cannula through which biological fluid is passed.

Figure 18B:
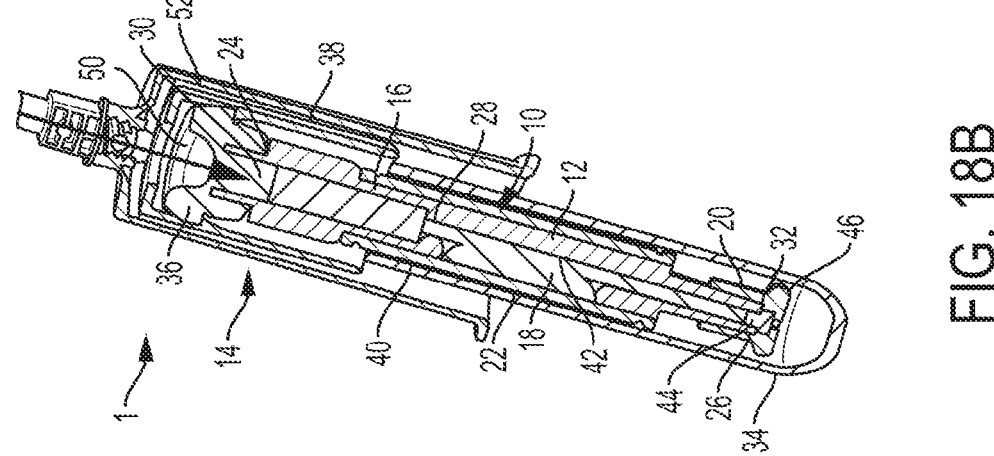
FIG. 18B is a partial cross-sectional perspective view of a biological fluid collection device, wherein a biological fluid sample is flowing into the collection module through a tube holder in accordance with an embodiment of the present invention.
Figure 18A:
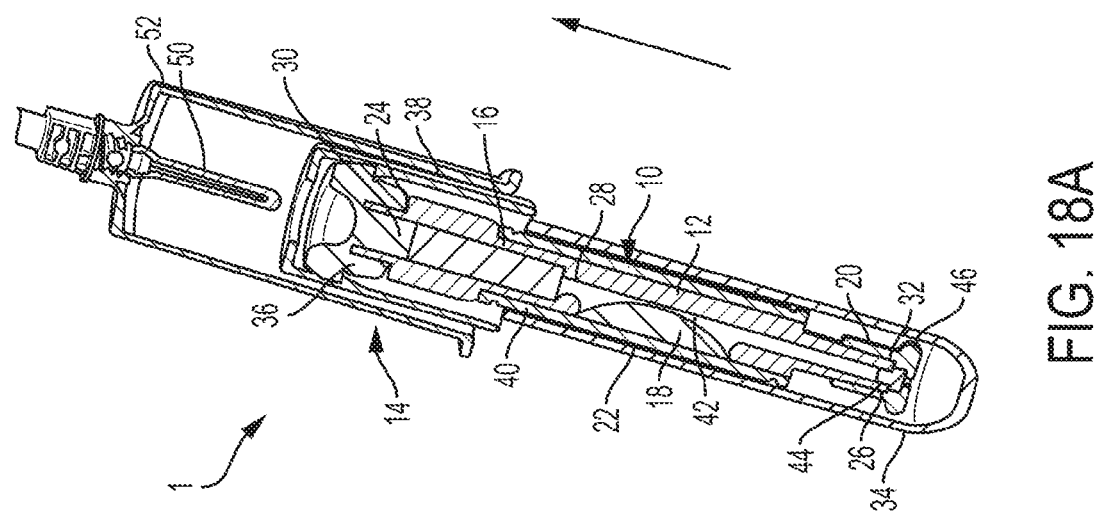
FIG. 18A is a partial cross-sectional perspective view of a biological fluid collection device being inserted into a tube holder in accordance with an embodiment of the present invention.
Figure 18D:
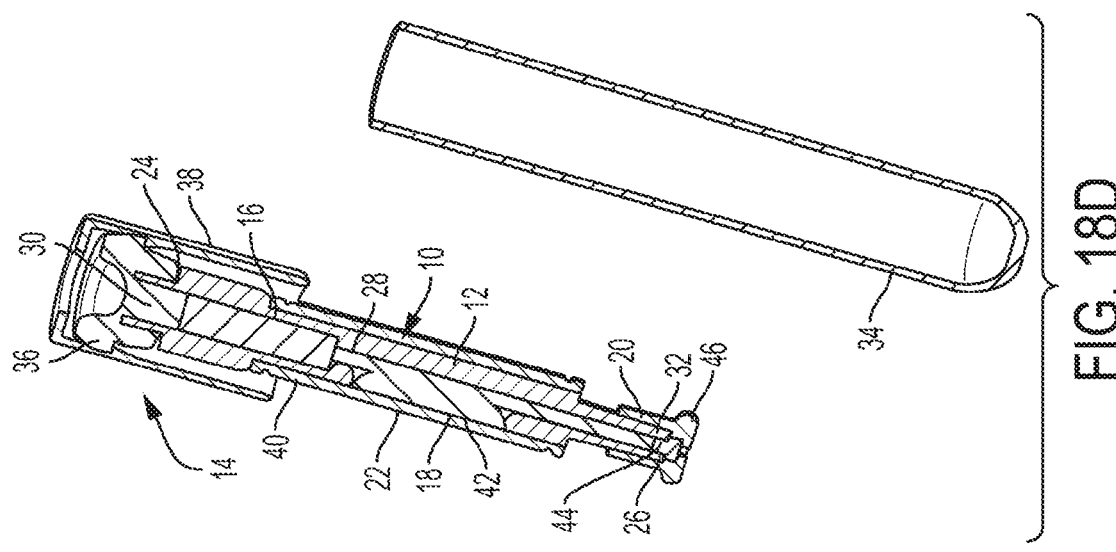
FIG. 18D is a partial cross-sectional perspective view of a collection module of a biological fluid collection device removed from an outer housing in accordance with an embodiment of the present invention.
Figure 18C:
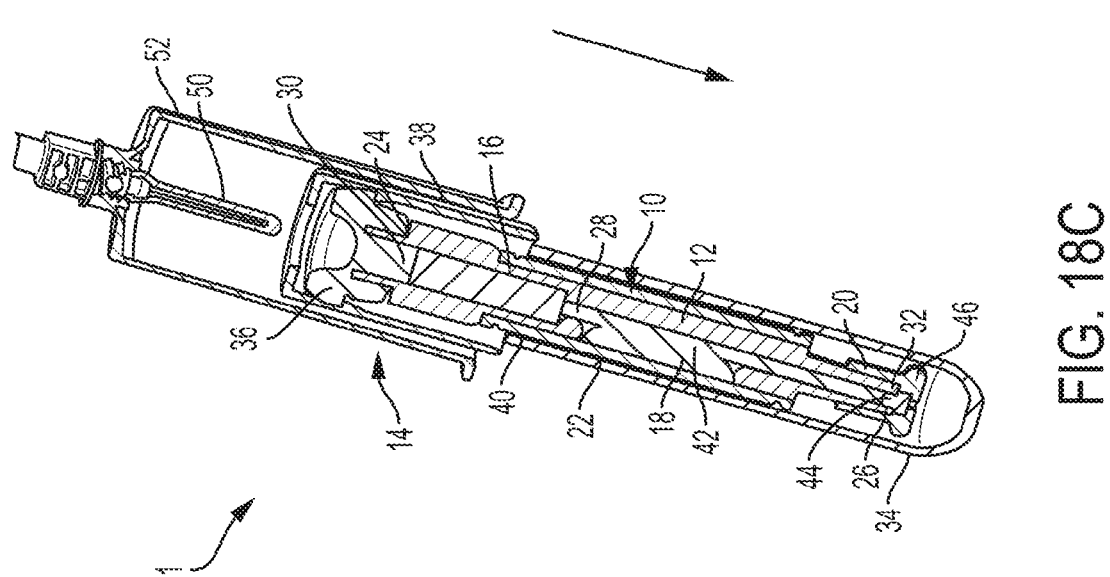
FIG. 18C is a partial cross-sectional perspective view of a biological fluid collection device being removed from a tube holder in accordance with an embodiment of the present invention.

The biological fluid sample is pulled into the passageway 28 of the housing 12 from the conventional tube holder 52 by the draw of the vacuum contained in the outer housing 34 (FIG. 18B). The blood sample fills the entire passageway 28 by first entering the mixing chamber 16 and subsequently the holding chamber 18 and expels any air present in the passageway 28 into the outer housing 34. As described above, the biological fluid sample is exposed to, and mixed with, an anticoagulant or other additive as it passes through the mixing chamber 16. The cap 20 stops the collection of the blood sample when the passageway 28, mixing chamber 16, and holding chamber 18 of the collection module 10 has been fully filled. The venting plug 44 of the cap 20 prevents blood from passing into the outer housing 34.

Once sample collection is complete, the outer housing 34 including the collection module 10 is separated from the tube holder 52 (FIG. 18C), and then the outer housing 34 is separated from the collection module 10 (FIG. 18D) by removing the closure 14, which is still attached to the collection module 10, from the outer housing 34. Removal of the closure 14 may be accomplished by the user grasping both the outer shield 38 of the closure 14 and the outer housing 34 and pulling or twisting them in opposite directions.

Once the collection module 10 is separated from the outer housing 34, the cap 20 may then be removed from the collection module 10 (FIG. 18F) exposing the second end 26 of the housing 12. Removal may be accomplished by the user grasping the flange 46 and pulling the cap 20 from the housing 12. The blood sample is held within the passageway 28 of the housing 12 by capillary action after removal of the cap 20. Alternatively, removal of the cap 20 may occur upon removal of the collection module 10 from the outer housing 34. In this configuration, the cap 20 is restrained within the outer housing 34 by the interaction of the flange 46 and corresponding recess of the outer housing wall. In one embodiment, the cap 20 may be connected to the outer housing 34 so that the outer housing 34 and the cap 20 are removed in one step.

Figure 18F:
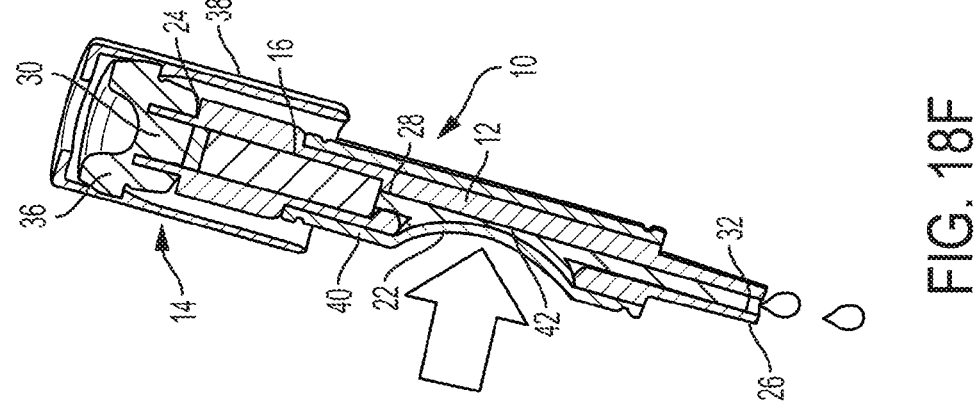
FIG. 18F is a partial cross-sectional perspective view of an activation member of a collection module of a biological fluid collection device being activated to dispense biological fluid from the collection module in accordance with an embodiment of the present invention.
Figure 18E:
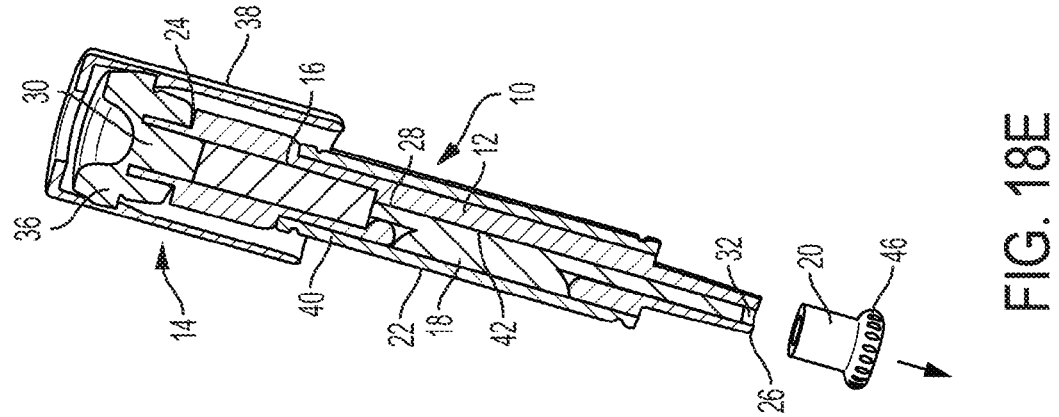
FIG. 18E is a partial cross-sectional perspective view of a cap being removed from a collection module of a biological fluid collection device in accordance with an embodiment of the present invention.

The blood sample is then dispensed from the collection module 10 by activation of the activation member 22, such as applying an inward pressure in the direction of the arrow on the portion of the elastic sleeve 40 covering the holding chamber 18 forcing the blood sample out of the holding chamber 18 and through the sample dispensing opening 32 (FIG. 18F). In this manner, the blood sample may be transferred to a device intended to analyze the sample, such as a point-of-care testing device, such as a cartridge tester or via a port while minimizing the exposure of the medical practitioner to the blood sample.

While a portion of the elastic sleeve 40 is shown and described as partially defining the holding chamber 18 and acting as the activation member 22 for dispensing the blood sample from the collection module 10, other alternative arrangements for achieving the same result are envisioned. For example, the holding chamber 18 may be wholly defined by the housing 12 and a separate activation device engaged with the holding chamber 18 may be activated to dispense the blood sample, including but not limited to, a plunger, push button, a slide, and the like.

Figure 17:
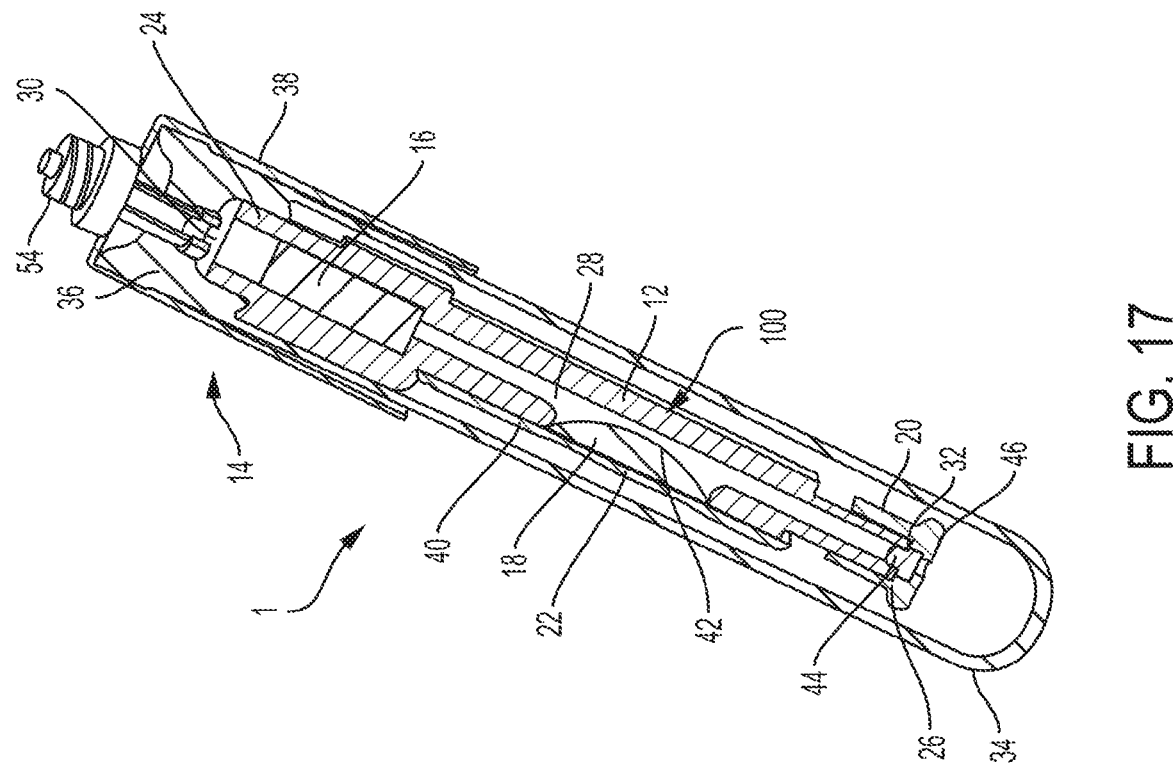
FIG. 17 is a partial cross-sectional perspective view of the biological fluid collection device of FIG. 16 in accordance with an embodiment of the present invention.
Figure 16:
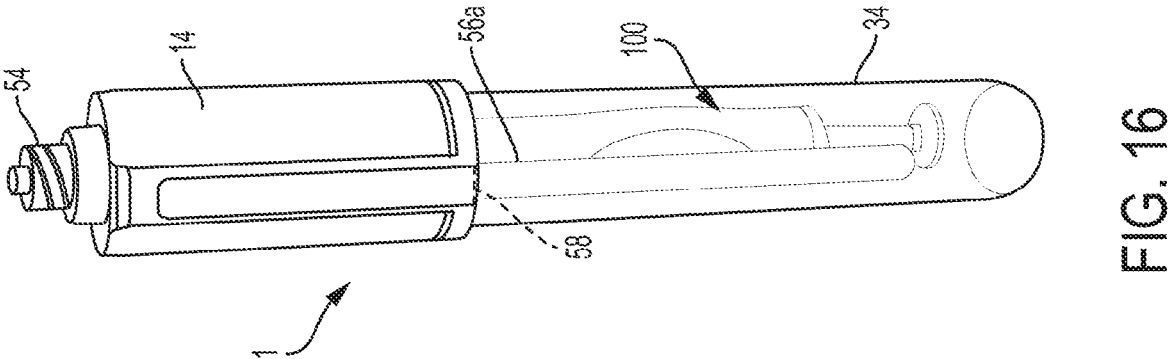
FIG. 16 is a perspective view of a biological fluid collection device having a collection module disposed within an outer housing in accordance with an embodiment of the present invention.

In another embodiment, shown in FIGS. 16 and 17, the closure 14 may have a luer lock connection 54 passing through the stopper 36. This configuration is useful when drawing a blood sample from an artery where no vacuum is necessary to pull the blood sample into a collection module 100 (FIGS. 16 and 17) such as is necessary with venous blood collection. The collection module 100 is used in the same manner as the collection module 10 except that the luer lock connection 54 is used to connect the collection module 100 to a wing set or other collection means have a mating luer lock connection to introduce the blood sample into the passageway 28.

The collection modules 10, 100 may also be used without the outer housing 34. In the case of the collection module 10, a syringe or other power source may be used to draw the sample into the collection module 10. Further, while the discussion herein has focused on the use of the collection modules 10, 100 to collect a blood sample and mix it with an anticoagulant or other additive, the collection modules 10, 100 may also be used to collect any liquid sample, such as other bodily fluids, or may be used to provide mixing and dispensing of a sample that was already collected by another means.

Figure 21:
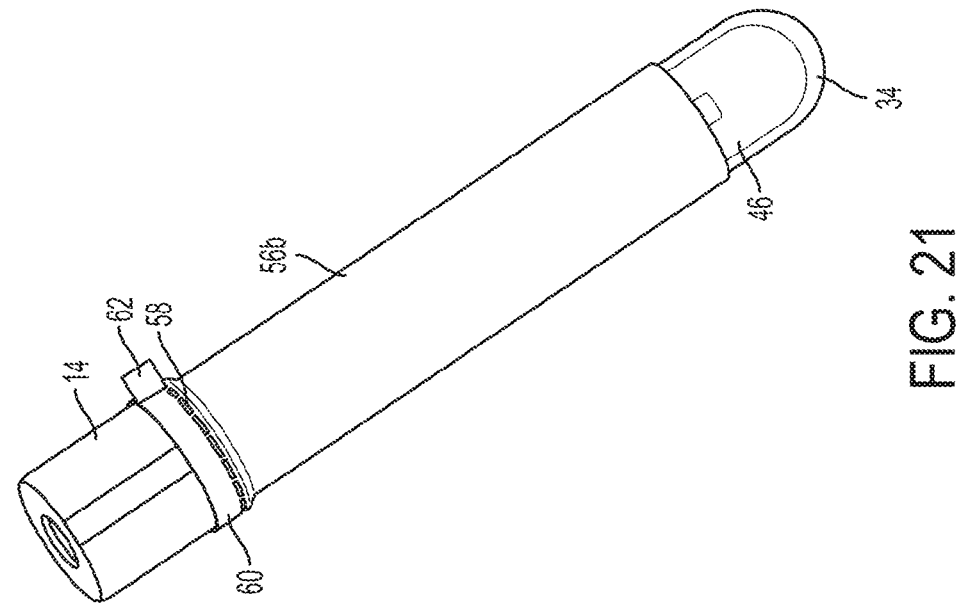
FIG. 21 is a perspective view of a biological fluid collection device in accordance with an embodiment of the present invention.

In a further configuration, the collection module 10 may include a label 56a, 56b adhered to both the closure 14 and the outer housing 34 that must be broken to remove the collection module 10 from the outer housing 34. As shown in FIGS. 14-17, the label 56a may be a strip that only extends along a portion of the outer perimeter of the closure 14 and the outer housing 34. Twisting the closure 14 with respect to the outer housing 34 breaks the strip at the point where it transitions from the outer housing 34 to the closure 14. Perforations 58 may be provided in the label 56a at the point where it transitions from the outer housing 34 to the closure 14 to assist the strip in breaking when the closure 14 is twisted. Alternatively, as shown in FIG. 21, the label 56b may surround the entire perimeter of both the closure 14 and the outer housing 34. Perforations 58 are provided in the label 56b at the point where it transitions from the outer housing 34 to the closure 14 forming a band 60 around the closure 14 that may be separated from the portion of the label 56b surrounding the outer housing 34. Removal of the band 60 from the closure 14 allows the closure 14 to be removed from the outer housing 34. A pull tab 62 may be provided on the band 60 to assist in separating it from the portion of the label 56b surrounding the outer housing 34.

As discussed above, referring to FIGS. 1-5, a cap 20 of the present disclosure includes a venting plug 44 that allows air to pass therethrough and prevents a blood sample from passing therethrough. In one embodiment, the venting plug 44 is a porous plug. In one embodiment, the cap 20 includes a venting plug 44 that includes a carboxymethylcellulose additive.

A cap of the present disclosure is compatible with any collection chamber of a biological fluid collection device, and the cap of the present disclosure may be used to vent air prior to sealing liquids within the chamber. For example, a cap of the present disclosure is compatible with the biological fluid collection device shown in FIGS. 14-18F. The cap of the present disclosure is also compatible with the biological fluid collection device shown in FIGS. 1 and 2. Furthermore, the cap of the present disclosure is also compatible with other biological fluid collection devices having a collection chamber.

Carboxymethylcellulose is a "self-sealing" additive that swells when it comes into contact with a liquid. When this additive is placed within a porous material, particularly a hydrophobic material, it allows air to vent prior to swelling shut when liquid reaches the carboxymethylcellulose. This prevents liquid from escaping a collection chamber of the biological fluid collection device. Carboxymethylcellulose can cause analyte bias (typically Ca$^{2+}$, Na$^+$, K$^+$) in small blood sample volumes (<5 mL).

If membranes having a carboxymethylcellulose additive are exposed to blood, or liquids of interest, at a high surface area contact area to volume ratio can drastically impact analyte bias results in blood. The ion exchange that occurs between the carboxymethylcellulose additive and the ions in plasma can result in erroneous results.

In one embodiment, a cap 20 of the present disclosure limits analyte bias due to the interaction of plasma ions with the carboxymethylcellulose by reducing the contact area between the blood and the carboxymethylcellulose additive, e.g., decreasing radius.

In one embodiment, a cap 20 of the present disclosure limits analyte bias due to the interaction of plasma ions with the carboxymethylcellulose by increasing the path length between the blood and the carboxymethylcellulose additive, e.g., increasing a path length.

In one embodiment, a cap 20 of the present disclosure limits analyte bias due to the interaction of plasma ions with the carboxymethylcellulose by reducing diffusivity by introducing a porous material in front of the carboxymethylcellulose additive plug.

A cap 20 of the present disclosure reduces the rate at which a biasing ion can travel away from the carboxymethylcellulose source into the blood, i.e., measurement sample. A cap 20 of the present disclosure is of particular interest in small blood volumes (<5 mL) where the carboxymethylcellulose additive can drastically impact ion concentrations.

Referring to FIGS. 1-5, the cap 20 includes a cap body 70 and a venting plug 44. In one embodiment, the cap body 70 defines a first chamber 72 having a first diameter D1, a second chamber 74 having a second diameter D2, and a third chamber 76 having a third diameter D3. In one embodiment, the second chamber 74 is between the first chamber 72 and the third chamber 76. In one embodiment, the second diameter D2 is less than the first diameter D1. In one embodiment, the second diameter D2 is less than the third diameter D3. In one embodiment, the first diameter D1 is less than the third diameter D3. In one embodiment, the first diameter D1 is 1.016 mm, the second diameter D2 is 0.4 mm, and the third diameter D3 is 1.5 mm. In one embodiment, a length of the second chamber 74 is 1.6 mm and a length of the third chamber 76 is 3.5 mm.

By reducing the diameter of the second chamber 74, a cap 20 of the present disclosure limits analyte bias due to the interaction of plasma ions with the carboxymethylcellulose by reducing the contact area between the blood and the carboxymethylcellulose additive, e.g., decreasing radius.

In one embodiment, the venting plug 44 is disposed in the third chamber 76. In one embodiment, the venting plug 44 includes a carboxymethylcellulose additive. The venting plug 44 allows air to pass therethrough and prevents a blood sample from passing therethrough. In one embodiment, the venting plug 44 is a porous plug. The construction of the venting plug 44 allows air to pass through the cap 20 while preventing the blood sample from passing through the cap 20 and may include a hydrophobic filter. The venting plug 44 has selected air passing resistance that may be used to finely control the filling rate of the passageway 28. By varying the porosity of the plug, the velocity of the air flow out of the cap 20, and thus the velocity of the blood sample flow into the collection module 10, may be controlled.

Figure 5:
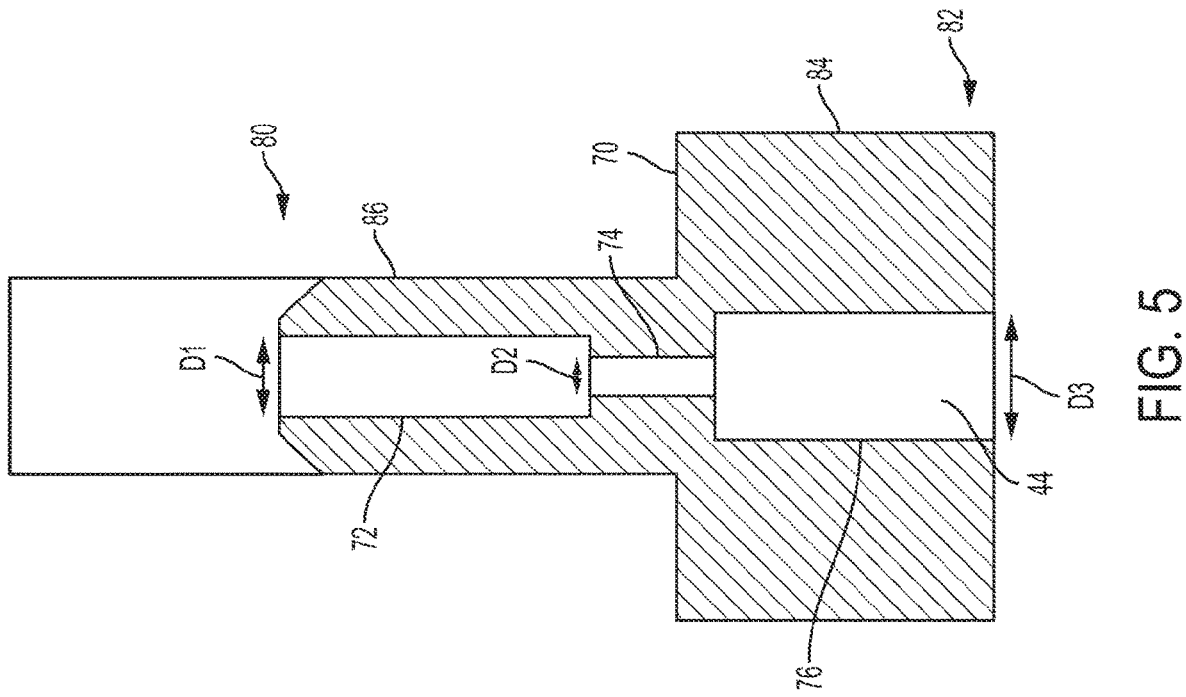
FIG. 5 is a cross-sectional view of a cap with venting plug in accordance with an embodiment of the present invention.
Figure 4:
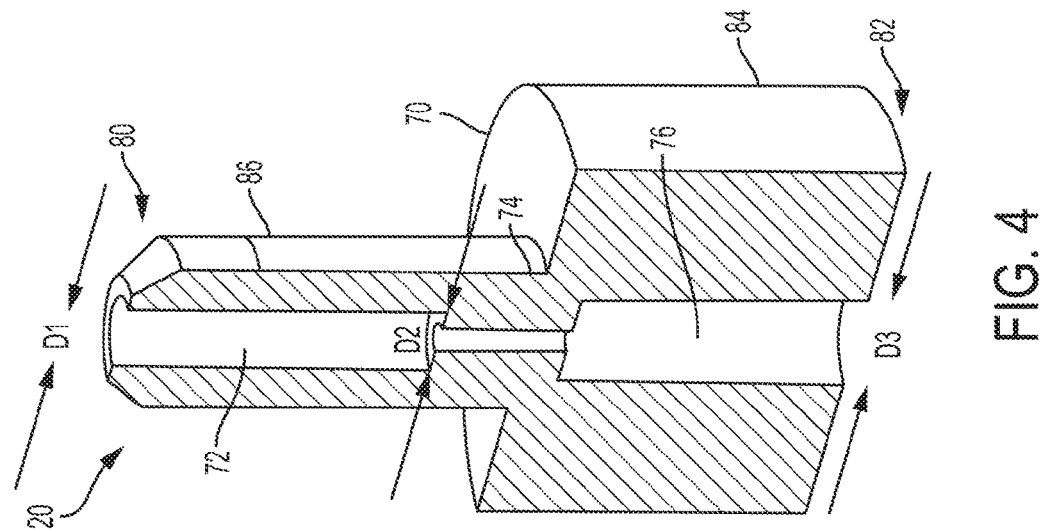
FIG. 4 is a cross-sectional view of a cap in accordance with an embodiment of the present invention.
Figures 6, 7, 8, 9:
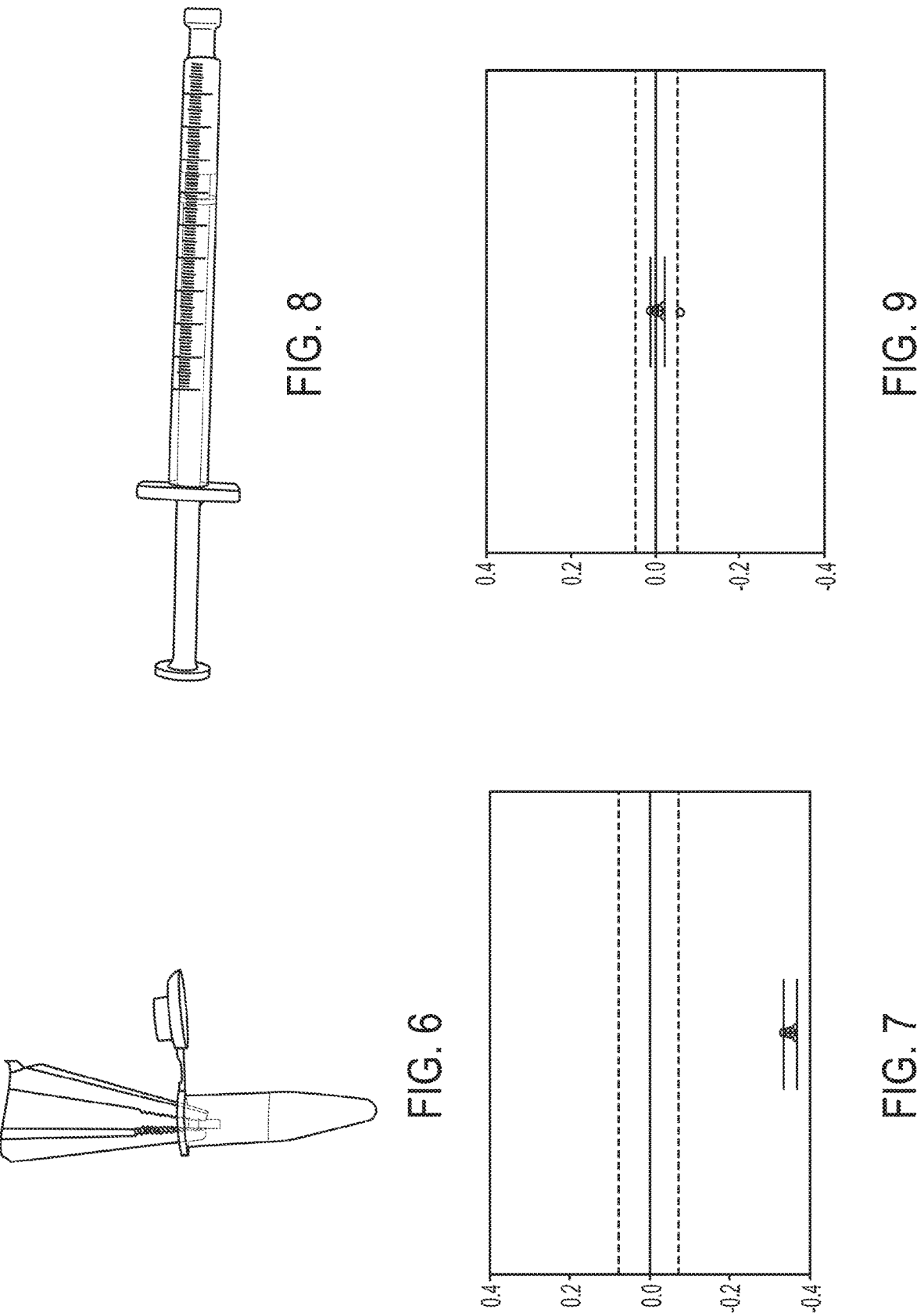
FIG. 6 is a perspective view of a cap in accordance with another embodiment of the present invention.
FIG. 7 is a graph of a cap of FIG. 6 in accordance with an embodiment of the present invention illustrating unit bias.
FIG. 8 is a perspective view of a cap in accordance with another embodiment of the present invention.
FIG. 9 is a graph of a cap of FIG. 8 in accordance with an embodiment of the present invention illustrating unit bias.

Referring to FIGS. 4 and 5, in one embodiment, the cap body 70 has a front end 80 and a back end 82. In one embodiment, the first chamber 72 is adjacent the front end 80 of the cap body 70 and the third chamber 76 is adjacent the back end 82 of the cap body 70.

In one embodiment, the cap body 70 includes a flange portion 84 and a plug portion 86. The flange portion 84 may be used to assist the user in removing the cap 20 from the housing 12. As shown in FIGS. 1 and 2, the flange portion 84 may have an outer diameter that is greater than the inner diameter of the outer housing 34 in which the collection module 10 may be placed. Alternatively, the flange portion 84 may have an outer diameter substantially equal to or less than the inner diameter of the outer housing 34. In addition, as shown in FIGS. 19 and 20, the flange 46, 84 may be made of an optically clear material and may have a convex outer diameter surface such that it magnifies the venting plug 44 area of the cap 20 allowing a medical practitioner to see when the blood sample has fully filled the passageway 28 and reached the cap 20. The flange 46, 84 may also be engaged with a recess of the interior wall of the outer housing 34 to restrain the cap 20 therewith.

In another embodiment, referring to FIGS. 11 and 12, a cap 120 of the present disclosure includes a first venting plug 122 and a second venting plug 124 including a carboxymethylcellulose additive.

Carboxymethylcellulose is a "self-sealing" additive that swells when it comes into contact with a liquid. When this additive is placed within a porous material, particularly a hydrophobic material, it allows air to vent prior to swelling shut when liquid reaches the carboxymethylcellulose. This prevents liquid from escaping a collection chamber of the biological fluid collection device. Carboxymethylcellulose can cause analyte bias (typically Ca$^{2+}$, Na$^+$, K$^+$) in small blood sample volumes (<5 mL).

If membranes having a carboxymethylcellulose additive are exposed to blood, or liquids of interest, at a high surface area contact area to volume ratio can drastically impact analyte bias results in blood. The ion exchange that occurs between the carboxymethylcellulose additive and the ions in plasma can result in erroneous results.

In one embodiment, a cap 120 of the present disclosure limits analyte bias due to the interaction of plasma ions with the carboxymethylcellulose by reducing diffusivity by introducing a porous material in front of the carboxymethylcellulose additive plug.

A cap 120 of the present disclosure reduces the rate at which a biasing ion can travel away from the carboxymethylcellulose source into the blood, i.e., measurement sample. A cap 120 of the present disclosure is of particular interest in small blood volumes (<5 mL) where the carboxymethylcellulose additive can drastically impact ion concentrations.

Referring to FIGS. 11 and 12, the cap 120 includes a cap body 170, a first venting plug 122, and a second venting plug 124. In one embodiment, the cap body 170 defines a chamber 172 having a first diameter D1. The cap body 170 includes a front end 180 and a back end 182. In one embodiment, the chamber 172 extends from the front end 180 to the back end 182.

In one embodiment, the cap body 170 includes a flange portion 184 and a plug portion 186. The flange portion 184 may be used to assist the user in removing the cap 20 from the housing 12. As shown in FIGS. 11 and 12, the flange portion 184 may have an outer diameter substantially equal to the inner diameter of the outer housing 34. In addition, as shown in FIGS. 19 and 20, the flange 46, 184 may be made of an optically clear material and may have a convex outer diameter surface such that it magnifies the venting plug area of the cap 120 allowing a medical practitioner to see when the blood sample has fully filled the passageway 28 and reached the cap 120. The flange 46, 184 may also be engaged with a recess of the interior wall of the outer housing 34 to restrain the cap 120 therewith.

In one embodiment, the first venting plug 122 is disposed in the chamber 172. In one embodiment, the second venting plug 124 includes a carboxymethylcellulose additive. In one embodiment, the first venting plug 122 is disposed between the second venting plug 124 and the front end 180 of the cap body 170.

The second venting plug 124 allows air to pass therethrough and prevents a blood sample from passing therethrough. In one embodiment, the first venting plug 122 is a porous plug. In one embodiment, the second venting plug 124 is a porous plug.

The construction of the second venting plug 124 allows air to pass through the cap 120 while preventing the blood sample from passing through the cap 120 and may include a hydrophobic filter. The second venting plug 124 has selected air passing resistance that may be used to finely control the filling rate of the passageway 28. By varying the porosity of the plug, the velocity of the air flow out of the cap 120, and thus the velocity of the blood sample flow into the collection module 10, may be controlled.

Referring to FIG. 11, in one embodiment, the second venting plug 124 is a sheet 190 that covers a portion of the back end 182 of the cap body 170.

Referring to FIG. 12, in one embodiment, the second venting plug 124 is disposed in the chamber 172 of the cap body 170, wherein the first venting plug 122 is disposed between the second venting plug 124 and the front end 180 of the cap body 170.

By including a first venting plug 122 upstream of the second venting plug 124 having a carboxymethylcellulose additive, a cap 120 of the present disclosure limits analyte bias due to the interaction of plasma ions with the carboxymethylcellulose by reducing diffusivity by introducing a porous material in front of the carboxymethylcellulose additive plug.

Diffusion through a porous material can be reduced by decreasing the material porosity or constrictivy and by increasing the tortuosity. In one embodiment, a cap having a first venting plug 122 and a second venting plug 124 having a carboxymethylcellulose additive works independently as shown in FIGS. 11 and 12.

In another embodiment, a cap having a first venting plug 122 and a second venting plug 124 having a carboxymethylcellulose additive as shown in FIGS. 11 and 12 can be combined with a cap body 70 defining a first chamber 72 having a first diameter D1, a second chamber 74 having a second diameter D2, and a third chamber 76 having a third diameter D3 as shown in FIG. 4. Both embodiments provide the advantageous result of reducing the rate at which analyte bias occurs in samples sealed with carboxymethylcellulose porous plugs.

Referring to FIG. 13, in another embodiment, a cap 220 of the present disclosure includes a first venting plug 222 including a carboxymethylcellulose additive and a second venting plug 224 including a carboxymethylcellulose additive.

Carboxymethylcellulose is a "self-sealing" additive that swells when it comes into contact with a liquid. When this additive is placed within a porous material, particularly a hydrophobic material, it allows air to vent prior to swelling shut when liquid reaches the carboxymethylcellulose. This prevents liquid from escaping a collection chamber of the biological fluid collection device. Carboxymethylcellulose can cause analyte bias (typically $Ca^{2+}$, $Na^+$, $K^+$) in small blood sample volumes (<5 mL).

If membranes having a carboxymethylcellulose additive are exposed to blood, or liquids of interest, at a high surface area contact area to volume ratio can drastically impact analyte bias results in blood. The ion exchange that occurs between the carboxymethylcellulose additive and the ions in plasma can result in erroneous results.

In one embodiment, a cap 220 of the present disclosure limits analyte bias due to the interaction of plasma ions with the carboxymethylcellulose by reducing the contact area between the blood and the carboxymethylcellulose additive, e.g., decreasing radius.

In one embodiment, a cap 220 of the present disclosure limits analyte bias due to the interaction of plasma ions with the carboxymethylcellulose by increasing the path length between the blood and the carboxymethylcellulose additive, e.g., increasing a path length.

A cap 220 of the present disclosure reduces the rate at which a biasing ion can travel away from the carboxymethylcellulose source into the blood, i.e., measurement sample. A cap 220 of the present disclosure is of particular interest in small blood volumes (<5 mL) where the carboxymethylcellulose additive can drastically impact ion concentrations.

Referring to FIG. 13, the cap 220 includes a cap body 270, a first venting plug 222, and a second venting plug 224. In one embodiment, the cap body 270 defines a first chamber 272 having a first diameter D1, a second chamber 274 having a second diameter D2, and a pair of third chambers 276 having a third diameter D3. In one embodiment, the second chamber 274 is between the first chamber 272 and the third chambers 276. In one embodiment, the second diameter D2 is less than the first diameter D1. In one embodiment, the second diameter D2 is less than the third diameter D3.

By reducing the diameter of the second chamber 274, a cap 220 of the present disclosure limits analyte bias due to the interaction of plasma ions with the carboxymethylcellulose by reducing the contact area between the blood and the carboxymethylcellulose additive, e.g., decreasing radius.

Referring to FIG. 13, in one embodiment, the second chamber 274 includes a first channel 277, a second channel 278, and a third channel 279. In one embodiment, a first of the third chambers 276 is in communication with the first chamber 272 via the first channel 277 and the second channel 278 and a second of the third chambers 276 is in communication with the first chamber 272 via the first channel 277 and the third channel 279.

By having a second chamber 274 that extends a path length between the first chamber 272 and the third chambers 276 by including a first channel 277, a second channel 278, and a third channel 279, a cap 220 of the present disclosure limits analyte bias due to the interaction of plasma ions with the carboxymethylcellulose by increasing the path length between the blood and the carboxymethylcellulose additive, e.g., increasing a path length.

In one embodiment, the first venting plug 222 is disposed in a first of the third chambers 276. In one embodiment, the first venting plug 222 includes a carboxymethylcellulose additive. In one embodiment, the second venting plug 224 is disposed in a second of the third chambers 276. In one embodiment, the second venting plug 224 includes a carboxymethylcellulose additive.

The first venting plug 222 and the second venting plug 224 allow air to pass therethrough and prevents a blood sample from passing therethrough. In one embodiment, the first venting plug 222 is a porous plug. In one embodiment, the second venting plug 224 is a porous plug.

The construction of the first venting plug 222 and the second venting plug 224 allow air to pass through the cap 220 while preventing the blood sample from passing through the cap 220 and may include a hydrophobic filter. The first venting plug 222 and the second venting plug 224 each have selected air passing resistance that may be used to finely control the filling rate of the passageway 28. By varying the porosity of the plug, the velocity of the air flow out of the cap 220, and thus the velocity of the blood sample flow into the collection module 10, may be controlled.

The present disclosure provides, in one embodiment, a cap that limits analyte bias due to the interaction of plasma ions with the carboxymethylcellulose by reducing the contact area between the blood and the carboxymethylcellulose additive, e.g., decreasing radius.

The present disclosure provides, in one embodiment, a cap that limits analyte bias due to the interaction of plasma ions with the carboxymethylcellulose by increasing the path length between the blood and the carboxymethylcellulose additive, e.g., increasing a path length.

The present disclosure provides, in one embodiment, a cap that limits analyte bias due to the interaction of plasma ions with the carboxymethylcellulose by reducing diffusivity by introducing a porous material in front of the carboxymethylcellulose additive plug.

A cap of the present disclosure reduces the rate at which a biasing ion can travel away from the carboxymethylcellulose source into the blood, i.e., measurement sample. A cap of the present disclosure is of particular interest in small blood volumes (<5 mL) where the carboxymethylcellulose additive can drastically impact ion concentrations.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device, comprising:
a blood collection tube;
a stopper sealing an opening in the blood collection tube;
a collection module disposed within the blood collection tube, the collection module including a first end attached to the stopper, a second end opposite the first end and positioned within the blood collection tube, and a passageway extending therebetween; and
a cap body attached to the second end of the collection module within the blood collection tube, the cap body defining:
a plug portion at a front end of the cap body configured to reside within the passageway of the collection module,
a flange portion at a back end of the cap body, wherein the flange portion has an outer diameter greater than an outer diameter of the plug portion and is configured to abut the second end of the collection module,
a first chamber having a first diameter,
a second chamber having a second diameter, and
a third chamber having a third diameter, the second chamber disposed between the first chamber and the third chamber, wherein the first chamber includes a first opening at the front end of the cap body and the third chamber includes an opening at the back end of the cap body, wherein the first chamber is disposed within the plug portion, the second chamber is disposed within at least a portion of both the plug portion and the flange portion, and the third chamber is disposed within the flange portion; and
a venting plug disposed in the third chamber, the venting plug comprising a carboxymethylcellulose additive, wherein the venting plug is configured to permit air to flow from the passageway, through the cap body, and into the blood collection tube.

2. The biological fluid collection device of claim 1, wherein the second diameter is less than the first diameter, and wherein the second diameter is less than the third diameter.

3. The biological fluid collection device of claim 1, wherein the first diameter is less than the third diameter.

4. The biological fluid collection device of claim 1, wherein the first diameter is 1.016 mm, the second diameter is 0.4 mm, and the third diameter is 1.5 mm.

5. The biological fluid collection device of claim 1, wherein a length of the second chamber is 1.6 mm and a length of the third chamber is 3.5 mm.

6. The biological fluid collection device of claim 1, wherein the venting plug prevents a blood sample from passing therethrough, and wherein the cap body defines an air flow path from the first chamber to the second chamber, through the venting plug, and exiting the cap body through the third chamber.

7. The biological fluid collection device of claim 1, wherein the venting plug is a porous plug.

* * * * *